(12) United States Patent
Mojarrad et al.

(10) Patent No.: US 11,660,435 B2
(45) Date of Patent: May 30, 2023

(54) LIGHT-ACTIVATED ULTRASONIC DELIVERY AND MANIPULATION OF LIQUID MEDICATION FROM A DRUG RESERVOIR

(71) Applicant: AMGEN INC., Thousand Oaks, CA (US)

(72) Inventors: Mehran Mojarrad, Thousand Oaks, CA (US); Scott R. Gibson, Granada Hills, CA (US); Heejin Lee, Bedford, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 17/642,345

(22) PCT Filed: Oct. 5, 2020

(86) PCT No.: PCT/US2020/054254
§ 371 (c)(1),
(2) Date: Mar. 11, 2022

(87) PCT Pub. No.: WO2021/071780
PCT Pub. Date: Apr. 15, 2021

(65) Prior Publication Data
US 2022/0265975 A1 Aug. 25, 2022

Related U.S. Application Data

(60) Provisional application No. 62/936,022, filed on Nov. 15, 2019, provisional application No. 62/911,573, filed on Oct. 7, 2019.

(51) Int. Cl.
*A61M 31/00* (2006.01)
*A61M 5/14* (2006.01)
(Continued)

(52) U.S. Cl.
CPC .......... *A61M 31/00* (2013.01); *A61M 5/1407* (2013.01); *A61M 5/14248* (2013.01); *A61M 5/2053* (2013.01); *A61M 5/2066* (2013.01)

(58) Field of Classification Search
CPC ................ A61M 31/00; A61M 5/1407; A61M 5/14248; A61M 5/2053; A61M 5/2066;
(Continued)

(56) References Cited

U.S. PATENT DOCUMENTS

| 5,836,940 A | 11/1998 | Gregory |
| 6,029,518 A | 2/2000 | Oeftering |

(Continued)

FOREIGN PATENT DOCUMENTS

| KR | 20150100105 A | 9/2015 |
| WO | WO-2006077528 A2 | 7/2006 |
| WO | WO-2017021585 A1 | 2/2017 |

OTHER PUBLICATIONS

Gold-implanted plasmonic quartz plate as a launch pad for laser-driven photoacoustic microfluidic pumps—University of Houston. Apr. 2019. https://www.pnas.org/content/pnas/116/14/6580.full.pdf.

(Continued)

*Primary Examiner* — James D Ponton
(74) *Attorney, Agent, or Firm* — Marshall, Gerstein & Borun LLP

(57) ABSTRACT

The devices, assemblies, and methods described herein utilize photoacoustic principals to create a jet of fluid using a ultrasonic resonance member and a pulsed laser light beam. The ultrasonic resonance member is a treated substrate having an liquid interface surface in contact with a fluid. When a pulsed laser light beam is applied to the treated substrate, pressure is generated via induced ultrasonic waves to urge the fluid into a jet stream.

16 Claims, 4 Drawing Sheets

(51) Int. Cl.
*A61M 5/142* (2006.01)
*A61M 5/20* (2006.01)

(58) Field of Classification Search
CPC ................ A61M 5/30; A61M 31/002; A61M 2210/1042
See application file for complete search history.

(56) References Cited

U.S. PATENT DOCUMENTS

| | | | |
|---|---|---|---|
| 6,306,119 | B1 | 10/2001 | Weber et al. |
| 2009/0306633 | A1* | 12/2009 | Trovato ................ A61B 1/041 604/891.1 |
| 2015/0057505 | A1 | 2/2015 | Bangera et al. |
| 2018/0238358 | A1* | 8/2018 | Bao .................... G01N 21/1702 |

OTHER PUBLICATIONS

Micropumps and biomedical applications—A review. University of Houston. Apr. 2019. https://reader.elsevier.com/reader/sd/pii/S0167931718301527?token-BC85C9EF11C23DE63D34D2DB725932B8289659C1D7D84A85936601582ADFD615D06A9695F65CF731D9D737A471176802.

Researchers report new light-activated micro pump. Science Daily. Mar. 2019. www.sciencedaily.com/releases/2019/03/190311152741.htm.

"Gold-implanted plasmonic quartz plate as a launch pad for laser-driven photoacoustic microfluidic pumps", Yue, et al., Institute of Fundamental and Frontier Sciences, University of Electronic Science and Technology of China, https://www.pnas.org/content/pnas/116/14/6580.full.pdf, Apr. 2, 2019.

"Micropumps and biomedical applications—A review", Microelectronic Engineering, ScienceDirect Journals & Books, vol. 195, pp. 121-138, https://reader.elsevier.com/reader/sd/pii/S0167931718301527?token=BC85C9EF11C23DE63D34D2DB725932B8289659C1D7D84A85936601582ADFD615D06A9695F65CF731D9D737A471176802, Aug. 5, 2018.

"Reasearchers report new light-activated micro pump", www.sciencedaily.com/releases/2019/03/190311152741.htm, University of Houston, Mar. 14, 2019.

Written Opinion of International Searching Authority for International Application PCT/US2020/054254, dated Mar. 12, 2021.

International Search Report for International Application PCT/US2020/054254, dated Mar. 12, 2021.

* cited by examiner

LIGHT-ACTIVATED ULTRASONIC DELIVERY AND MANIPULATION OF LIQUID MEDICATION FROM A DRUG RESERVOIR

CROSS-REFERENCE TO RELATED APPLICATIONS

This is the United States national phase of International Patent Application No. PCT/US20/54254, filed Oct. 5, 2020, which claims priority to U.S. Provisional Patent Application No. 62/911,573, filed Oct. 7, 2019, and U.S. Provisional Patent Application No. 62/936,022, filed Nov. 15, 2019, the entire contents of each of which are hereby incorporated by reference herein.

FIELD OF THE DISCLOSURE

The present disclosure generally relates to drug delivery devices and, more particularly, to fluid dispensing assemblies for drug delivery devices.

BACKGROUND

Drugs can be administered through the use of drug delivery devices, such as autoinjectors or on-body injectors. Autoinjectors and on-body injectors may be used to help automate the injection and delivery or administration process, thereby simplifying the process for patients. In such devices, drug reservoirs can be made from glass or polymers and commonly contain a movable piston at one end. To achieve drug delivery, a drive mechanism pushes the piston through the reservoir to thereby force the drug out of the reservoir and into downstream components of the device. Drug delivery devices, which may be mass-produced, are often designed to minimize material, manufacturing, and storage costs to thereby reduce the total cost associated with a product. As such, designs and components to further reduce the footprint associated with necessary components can further the pursuit of lower costs.

SUMMARY

In accordance with a first aspect, an ingestible fluid delivery device is described that includes a body having one or more walls defining an interior and one or more outlets extending through the one or more walls. The device further includes an ultrasonic resonance member comprising a treated substrate having a fluid interface surface, a laser light source oriented to direct a pulsed light beam at the ultrasonic resonance member to urge a fluid therapeutic disposed within the interior into a jet stream, and a controller configured to control operation of the laser light source.

In some forms, the ultrasonic resonance member can be a plate, where the fluid interface surface is at least one of the main surfaces of the plate and the one or more outlets are aligned with the fluid interface surface across a portion of the interior. In other forms, the ultrasonic resonance member can be a rod, where the fluid interface surface is an annular outer surface of the rod and the one or more outlets are aligned radially outward of the rod across a portion of the interior.

In further forms, the device can include one or more of the following aspects: the device can include an isolator that extends across the interior of the body to divide the interior into a laser compartment and a fluid compartment, where the one or more outlets extend through the one or more walls into the fluid compartment and the laser light source is disposed within the laser compartment to direct a pulsed light beam at the ultrasonic resonance member through the isolator; the ultrasonic resonance member can be an isolator that extends across the interior of the body to divide the interior into a laser compartment and a fluid compartment, where the one or more outlets extend through the one or more walls into the fluid compartment and the laser light source is disposed within the laser compartment to direct a pulsed light beam at the isolator to urge the fluid therapeutic into a jet stream; the device can include a pH sensor and the controller can be configured to activate the laser light source in response to the pH sensor determining that the body is in an environment having a pH value above a predetermined threshold; the one or more outlets can be oriented along a longitudinal axis of the body to provide a luminal delivery of the fluid; or the one or more outlets can be oriented transverse to a longitudinal axis of the body to provide a radial delivery of the fluid.

In accordance with a second aspect, a drug delivery device is described that includes a container defining an interior with an outlet, an ultrasonic resonance member, and a laser light source oriented and configured to direct a pulsed light beam at the ultrasonic resonance member to urge a fluid therapeutic disposed within the container into a jet stream. The ultrasonic resonance member includes a treated substrate having a fluid interface surface in contact with the fluid therapeutic disposed within the interior, where the fluid interface surface is aligned with the outlet of the container.

In some forms, the ultrasonic resonance member can form a portion of the container or can be disposed within the interior of the container, where the container further comprises a window allowing the laser light source to direct a pulsed light beam through the window. Additionally, the laser light source can be oriented to direct a pulsed light beam along an axis generally parallel with the interface surface to take advantage of the waveguide property of container assuming it is made out of transparent and clear color media such as glass or special polymer suitable for long-term storage of the drug product.

In some forms, the container can be a first container and the ultrasonic resonance member can be a first ultrasonic resonance member. In these forms, the device can further include a second container defining an interior with an outlet and a second ultrasonic resonance member comprising a treated substrate having a fluid interface surface in contact with a fluid therapeutic disposed within the interior of the second container, where the fluid interface surface of the second ultrasonic resonance member is aligned with the outlet of the second container. Further, the outlets of the first and second containers are fluidly connected.

In some forms, the laser light source can be a first laser light source and the device can further include a second laser light source, where the second laser light source is oriented and configured to direct a pulsed light beam into the second ultrasonic resonance member to urge a fluid therapeutic disposed within the second container into a jet stream. In other forms, the first and second ultrasonic resonance members can be provided by a single-piece plate member and the laser light source can be oriented to direct a pulsed light beam along a longitudinal axis of the single-piece plate member to urge fluid therapeutics disposed within the first and second containers into jet streams to drive the fluid therapeutics through the outlets of the first and second containers, respectively, mixing the fluid therapeutics together and finally dispensing the mixture. In any of the above forms, the fluid therapeutics disposed within the interiors of the first and second containers can be a first fluid therapeutic and a second fluid therapeutic and vortices generated by the jet streams within the first and second containers can mix the first and second fluid therapeutics together to thereby deliver a mixture. Additionally, the first and second fluid therapeutics can be different from one another.

In some forms, the laser light source can include an array of laser light sources, where the array includes a plurality of laser light sources disposed about a circumference of the container and a central laser light source. The plurality of laser light sources can be configured to be sequentially activated around the circumference to create a vortex in a therapeutic fluid in the container and the central laser light source can be configured to direct the vortex toward the outlet.

In any of the above forms, vortices generated by the jet stream or jet streams created within the respective container can be utilized to reconstitute a lyophilized drug compound using a diluent solution.

In accordance with additional aspects, methods of operating the above drug delivery devices are described. In one form, a method for delivering a fluid therapeutic with an ingestible drug delivery device is described that includes providing an ingestible drug delivery device having a body including one or more walls defining an interior with a fluid therapeutic disposed therein, operating a laser light source disposed within the body with a controller of the ingestible drug delivery device to direct a pulsed light beam at an ultrasonic resonance member, creating a jet stream of the fluid therapeutic at a fluid interface surface of the ultrasonic resonance member exposed within the container, and ejecting the fluid therapeutic out through one or more outlets aligned with the fluid interface surface with the jet stream.

According to some forms, the method can include one or more of the following aspects: operating the laser light source to direct a pulsed light beam at the ultrasonic resonance member can include operating the laser light source to direct a pulsed light beam at an ultrasonic resonance member having a plate body with the fluid interface surface comprising opposite main surfaces of the plate body; operating the laser light source to direct a pulsed light beam at the ultrasonic resonance member can include operating the laser light source to direct a pulsed light beam at an ultrasonic resonance member having a rod body with the fluid interface surface comprising an annular surface of the rod body; ejecting the fluid therapeutic out through the one or more outlets aligned with the fluid interface surface with the jet stream comprises ejecting the fluid therapeutic out through one or more radial outlets oriented transverse to a longitudinal axis of the body; or the method can include determining a pH of an environment in which the body is located and operating the laser light source disposed within the body with the controller of the ingestible drug delivery device can include operating the laser light source disposed within the body with the controller in response to determining that the pH of the environment is over than a predetermined threshold.

DETAILED DESCRIPTION

Figure 1:
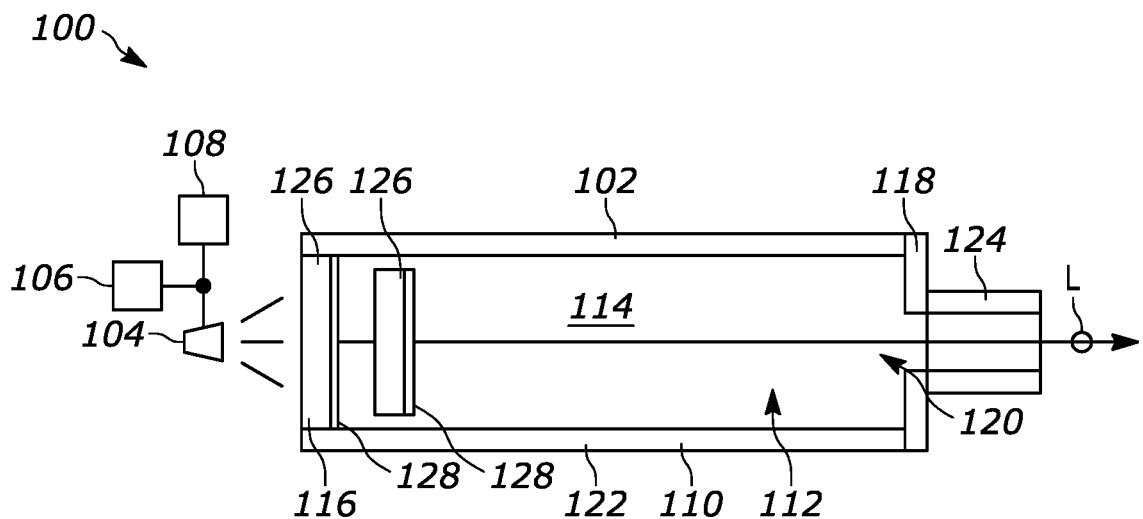
FIG. 1 is a cross-sectional view of a first example fluid delivery assembly including a container having an ultrasonic resonance member and a laser light source in accordance with various embodiments.

The devices, assemblies, and methods described herein utilize photoacoustic principals to urge a fluid into a jet stream using an ultrasonic resonance member and a pulsed laser light beam. The ultrasonic resonance member is a treated substrate, which in some versions can be a treated glass substrate, having a liquid interface surface in contact with a fluid. When a pulsed laser light beam is applied to the treated substrate, pressure is generated via induced ultrasonic waves to urge the fluid into a jet stream. By strategically positioning the treated substrate in or on a fluid container and controlling the laser light source pulse rate, location, and power levels, the pressure and direction of the fluid jet stream can be manipulated for a desired action, including drug delivery, fluid mixing, and fluid manipulation. For example, utilizing any of the assemblies described herein, the fluid therapeutic can include a diluent solution and the fluid jet stream can be utilized to reconstitute a lyophilized drug compound, whether in the respective container with the ultrasonic resonance member or downstream therefrom in a subsequent conduit or container. Advantageously, the assemblies described herein provide fluid movement and delivery without any moving parts, utilizing components at microelectromechanical systems (MEMS) scale.

In some versions, including when the substrate may be glass, the treatment of the glass substrate can involve ion implantation of precious metals, such as gold, platinum, palladium, or similar metals (or electron donor elements, such as metals, transition metals, post-transition metals, and semiconductors, or combinations thereof) on a surface of the glass substrate. In one example, the treated glass substrate can be made of quartz crystalline implanted with precious metals ions or electron donor elements ions. For example, for a 500 μm thick quartz crystalline substrate, the depth of ion implanted gold can be at a relatively shallow depth of about 50 nm. Of course, the implantation depth can depend on the thickness of the glass substrate. As such, for thicker glass substrates, relatively deeper and denser implants may be utilized to provide stronger effects.

With these compositions, when a pulsed laser light beam of a predetermined wavelength is emitted into the treated glass substrate, the glass substrate becomes active and generates ultrasonic waves to thereby manipulate a fluid in contact with a fluid interface surface of the treated glass substrate. The fluid interface surface of the treated glass substrate will resonate at the predetermined light wavelength, which corresponds to the absorption of the light being at a maximum level associated with the specific substrate geometry and selected ion implanted metal. This effect causes a local ultrasonic resonance at the fluid interface surface and produces an ultrasonic wave within a fluid in contact with the surface. The resulting pressure of the ultrasonic wave depends on the pulse rate and the power amplitude of the laser light. The generated ultrasonic waves urge the fluid into a jet stream with enough pressure and velocity for liquid transport out of a container in a desired direction. For drug delivery devices and methods, the fluid can be a fluid therapeutic, which can be driven by the jet stream out of a drug container and/or directional movement within channels and fluidic paths within the drug delivery device. In additional or alternative form, the fluid jet stream can be directed to achieve mixing of multiple fluids, such as with the reconstitution of lyophilized drug compounds.

As indicated above, several inputs factor into the pressure generated in the fluid and the resulting velocity of the jet stream. In general, the factors can include: a depth of the implanted ions, a density of the implanted ions, a type of metal or electron donor material implanted into the glass substrate, a pulse rate of the laser light source, a pulse width of the laser light source, a power amplitude of the laser light source, a wavelength of the laser light source, and photonic absorption properties of the glass substrate. These properties combine to determine a maximum optical absorption of the treated glass substrate leading to plasmonic resonance of the implanted metal clusters and nanoparticles, which in turn results in an ultrasonic jet stream in the fluid in contact with the fluid interface surface of the treated glass substrate.

Example fluid delivery assemblies utilizing the above configurations are shown in FIGS. 1 to 6. In first forms shown in FIGS. 1 and 2, a fluid delivery assembly 100 that includes a container 102 and a laser light source 104 powered by a suitable power source 106 and operated by a controller 108. The container 102 has a tubular configuration with one or more walls 110 defining an interior 112 for reception of a fluid therapeutic 114. In the illustrated form, the container 102 has a cylindrical configuration, such that the one or more walls 110 include a first end wall 116, an opposite, second end wall 118 having an outlet opening 120 extending therethrough, and a sidewall 122 extending between the end walls 116, 118. If desired, the container 102 can include a neck portion 124 extending around the outlet opening 120 and away from the second end wall 118.

The container 102 further includes an ultrasonic resonance member 126 having a fluid interface surface 128 exposed to the container interior 112 and in contact with the fluid therapeutic 114 therein. Advantageously, the direction of the jet stream created within the fluid therapeutic 114 upon application of the pulsed laser light beam is independent of the specific orientation of the laser light source 104 relative to the ultrasonic resonance member 126. Rather, the jet stream is always formed in a direction perpendicular to the fluid interface surface 128.

As such, the assembly 100 can position the laser light source 104 in any desirable position relative to the ultrasonic resonance member 126, as long as a pulsed laser light beam has a clear path to the ultrasonic resonance member 126. In a first form, shown in FIG. 1, the laser light source 104 is oriented to project light along a central axis L of the outlet opening 120, which in the illustrated from, is coincident with a longitudinal axis of the container 102. In a second form, shown in FIG. 2, the laser light source 104 is oriented to project light along a path generally transverse to the central axis L of the outlet opening 120 and the longitudinal axis of the container 102. For example, the laser light source 104 can be oriented to project light along a path perpendicular to the central axis L or can be oriented to project light along a path at an acute or obtuse angle with respect to the central axis L. The configuration of the second form can utilize a waveguide or a light-piping effect to activate the treated glass substrate and generate the ultrasonic effect. The second form can advantageously result in space saving layouts for drug delivery devices, described in more detail below, that may have limited longitudinal space, but with available space lateral to the container 102.

So configured, the ultrasonic resonance member 126 can be oriented so that the fluid interface surface 128 is disposed across the interior 112 from the outlet opening 120, with the fluid interface surface 128 extending generally perpendicular to a central axis L of the outlet opening 120, such that a created jet stream flows directly to and through the outlet opening 120. In the first form of FIG. 1, the first end wall 116 can be or can include the ultrasonic resonance member 126. Due to the orientation of the laser light source 104, the end wall 116 can be received within the sidewall 122. In the second form of FIG. 2, the ultrasonic resonance member 126 forms the end wall 116 and is mounted on an end of the sidewall 122, such that the ultrasonic resonance member 126 is accessible by a pulsed laser light beam generated laterally to the side of the container 102. Alternatively, as shown in FIG. 1, an alternative the ultrasonic resonance member 126 can be disposed within the container interior 112 rather than forming a portion of the one or more walls 110. In this form, at least a portion or window of the one or more walls 110, such as the end wall 116 or sidewall 122 can be transparent to allow a pulsed light beam to be projected therethrough. In this configuration, the resonant member 126 can be in any orientation desired to generate ultrasonic fluid jet streams suitable for fluid manipulation, such as generating vortices, assuming there is a means by which to wobble or to tilt at any elevation angle and rotate at any azimuth angle respectively of the resonant member 126 in the container interior 112. The reason for this phenomenon is that the ultrasonic jet stream is always perpendicular to the planar surfaces of the fluid interface 128 of the resonant member 126. The generated vortices could be used, for example, to mix and agitate the fluid 114, especially for reconstitution applications of lyophilized compounds when mixing with a diluent solution or in the case of mixing two or more therapeutics in the container interior 112.

Figure 2:
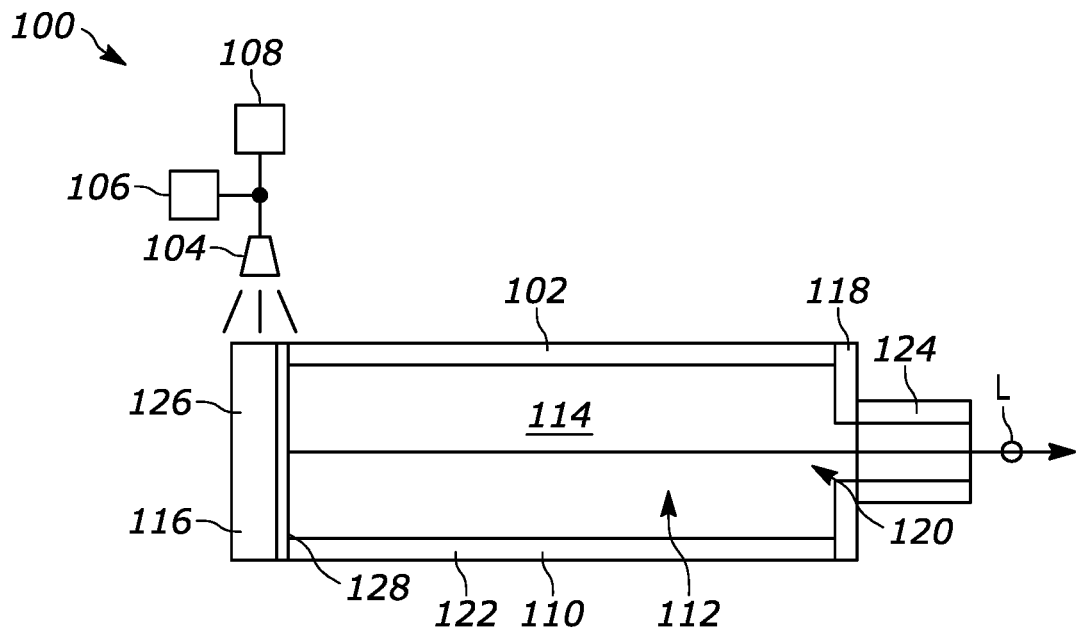
FIG. 2 is a cross-sectional view of a second example fluid delivery assembly including a container having an ultrasonic resonance member and a laser light source in accordance with various embodiments.
Figure 3:
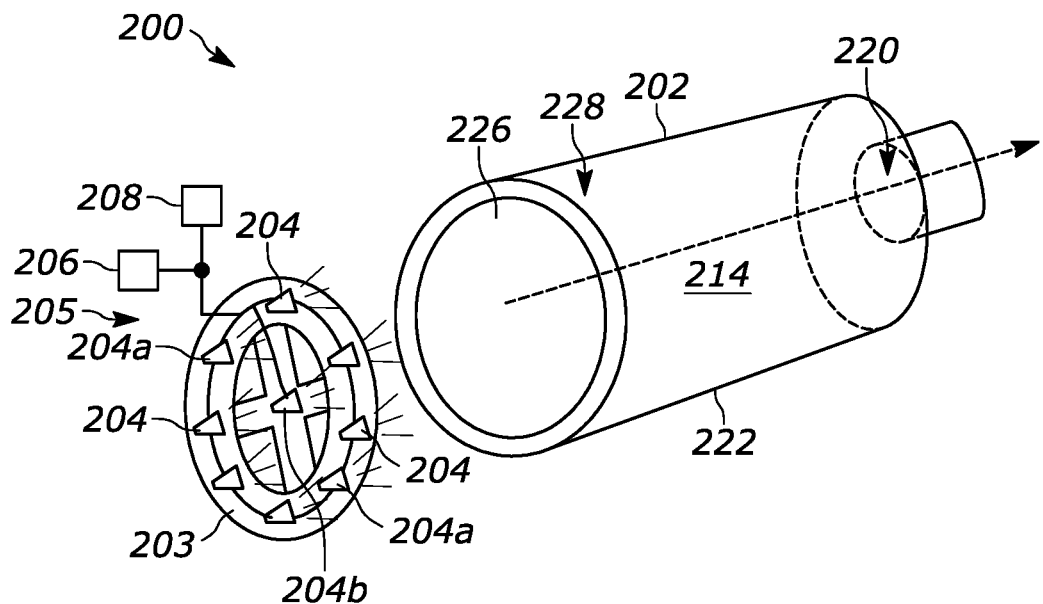
FIG. 3 is a cross-sectional view of a third example fluid delivery assembly including a container having an ultrasonic resonance member and an array of laser light sources in accordance with various embodiments.

A third example assembly 200 is shown in FIG. 3 having a container 202, which can be configured similarly to the containers 102 described with reference to FIGS. 1 and 2. Rather than a single laser light source 104 as shown in FIG. 1, however, the assembly 200 of this form includes a base 203 with a plurality of laser sight sources 204 mounted thereto in an array 205. In the illustrated form, the array 205 includes outer light sources 204a disposed in a ring shape having a diameter smaller than an inner diameter of a sidewall 222 of the container 202. Further, the array 205 includes a central light source 204b disposed generally centrally within the ring of outer light sources 204a.

With this configuration, a controller 208 can control power from a power source 206 to first selectively energize each of the outer light sources 204a in circular direction, such as clockwise or counterclockwise. The sequential activation of the outer light sources 204a creates a ring of jet streams within a fluid therapeutic 214 within the container 202 in contact with a fluid interface surface 228 of an ultrasonic resonance member 226, which results in the formation of a vortex. Thereafter, the controller 208 controls power from the power source 206 to energize the central light source 204b to urge the fluid therapeutic 214 into a central jet stream to thereby drive the vortex towards and out through an outlet opening 220 of the container 204. This configuration is particularly suitable for a fluid therapeutic 214 having a high viscosity by utilizing the additive pressure effect generated by the plurality of light sources 204. For example, the assembly 200 can include any number of outer light sources 204a, such as eight as shown, four to seven, or more than eight.

Figure 4:
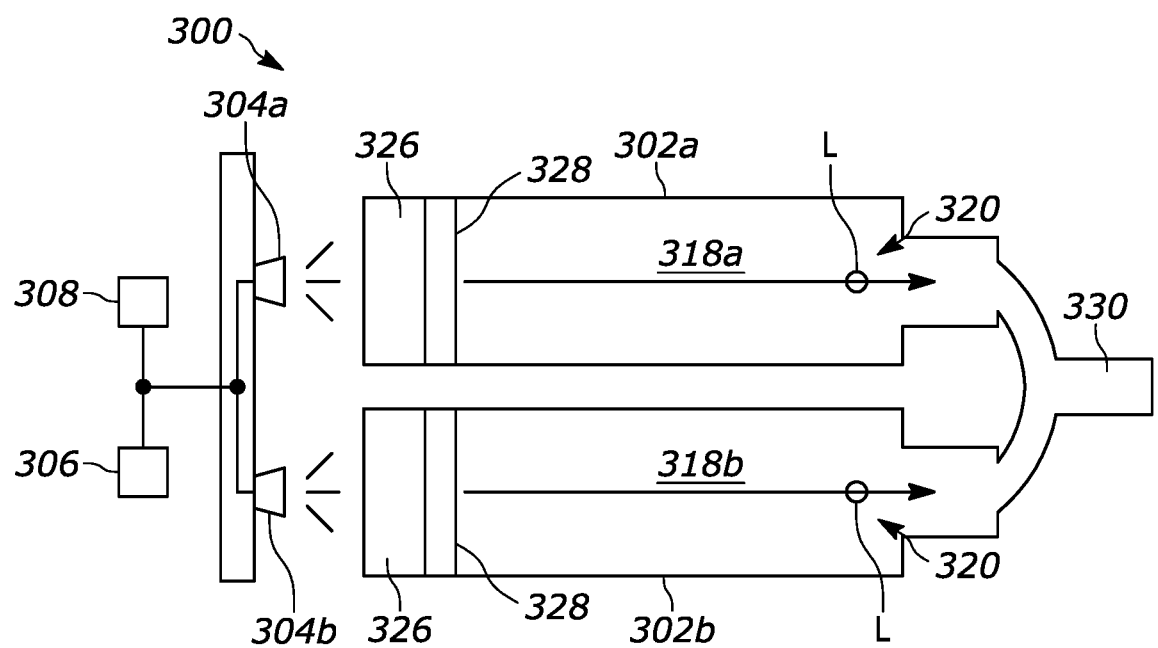
FIG. 4 is a cross-sectional view of a fourth example fluid delivery assembly including first and second containers each having an ultrasonic resonance member and first and second laser light sources in accordance with various embodiments.
Figure 5:
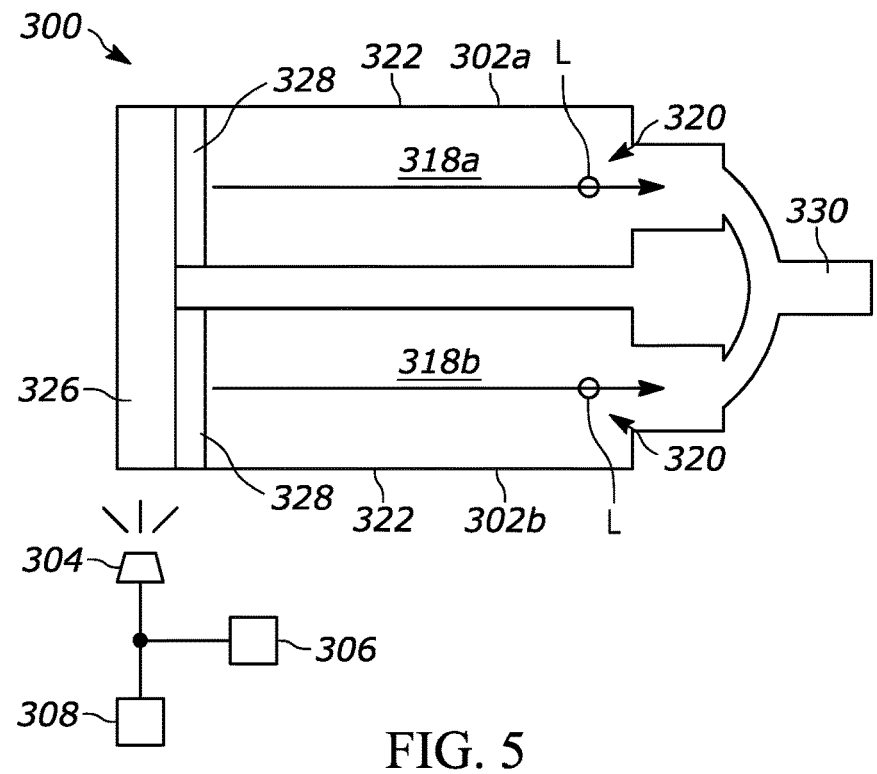
FIG. 5 is a cross-sectional view of a fifth example fluid delivery assembly including first and second containers having a shared ultrasonic resonance member and a laser light source in accordance with various embodiments.

Fourth and fifth example assemblies 300 are shown in FIGS. 4 and 5 having first and second containers 302a, 302b, which can be configured similarly to the containers 102 described with reference to FIGS. 1 and 2. The first and second containers 302a, 302b can be utilized to deliver first and second fluid therapeutics 318a, 318b either simultaneously or in tandem. The first and second fluid therapeutics 318a, 318b can be the same therapeutic or different therapeutics. For example, the assemblies 300 can be utilized to mix the first and second fluid therapeutics 318a, 318b to deliver a mixture. Moreover, it will be understood that more than two containers can be utilized to store and dispense any desired number of fluid therapeutics.

In a first form, shown in FIG. 4, the assembly 300 includes first and second light sources 304a, 304b, where the light sources 304a, 304b are oriented to project light along central axes L of an outlet opening 320 of the respective first or second container 302a, 302b. As with the above form, the central axis L of the outlet opening 320 of each container 302a, 302b is coincident with a longitudinal axis of the container 302a, 302b. With this configuration, a controller 308 can control power from a power source 306 to selectively energize the light sources 304a, 304b to direct a pulsed light beam at ultrasonic resonance members 326 having fluid interface surfaces 328 to urge fluid therapeutics 318a, 318b in the first and second containers 302a, 302b into jet streams. Advantageously, the controller 308 can activate the light sources 304a, 304b sequentially to dispense one of the fluid therapeutics 318a, 318b before the other 318a, 318b or simultaneously to dispense the fluid therapeutics 318a, 318b at the same time for any desired drug dispensing profile. As shown, the outlet openings 320 can be fluidly connected together to dispense fluid through a combined conduit 330. With this configuration, simultaneous activation of the light sources 304a, 304b results in the fluid therapeutics 318a, 318b at least partially mixing together and being dispensed through the conduit 330.

In a second form, shown in FIG. 5, the assembly 300 can utilize a single laser light source 304 that is oriented to project light along a path generally perpendicular to central axes L of outlet openings 320 of respective first and second containers 302a, 302b. As shown, the containers 302a, 302b are configured as described above so that a longitudinal axis of each container 302a, 302b is coincident with the central axis L of the outlet opening 320. Further, the assembly 300 of this form can utilize a waveguide or a light-piping effect to activate the treated glass substrate and generate the ultrasonic effect in both containers 302a, 302b with a single-piece ultrasonic resonance member 326. As shown, the ultrasonic resonance member 326 can have a plate body having a lateral width to couple to ends of sidewalls 322 of both containers 302a, 302b. Similarly to the above forms, the ultrasonic resonance member 326 includes fluid interface surfaces 328 for each of the containers 302a, 302b that extend perpendicular to the central axes L of the outlet openings 320 and are aligned therewith. The second form can advantageously result in space saving layouts for drug delivery devices, described in more detail below, that may have limited longitudinal space, but with available space lateral to the containers 302a, 302b. As shown, the outlet openings 320 can be fluidly connected together to dispense fluid through a combined conduit 330. With this configuration, simultaneous activation of the light sources 304a, 304b results in the fluid therapeutics 318a, 318b at least partially mixing together and being dispensed through the conduit 330.

The above containers 102, 202, 302a, 302b can take any desired form for a fluid therapeutic. For example, the containers 102, 202, 302a, 302b can be a primary container or reservoir for a drug delivery device. In other suitable applications, the containers 102, 202, 302a, 302b can be provided in cassettes, microfluidic plates with included fluidic channels, and drug reservoirs or prefilled syringes for drug delivery devices.

Figure 6:
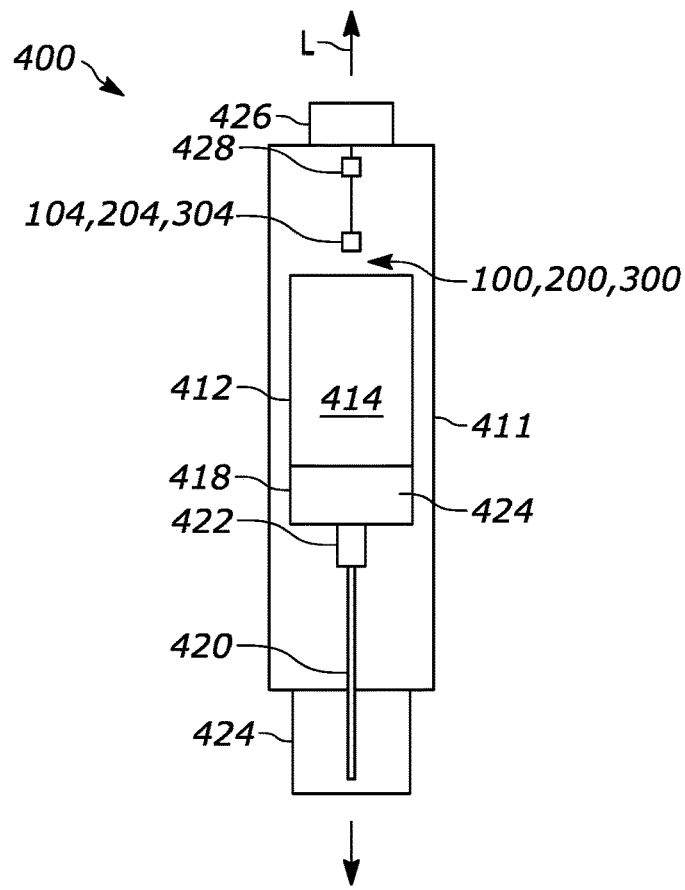
FIG. 6 is a diagrammatic view of an autoinjector drug delivery device.

In some versions as illustrated in FIG. 6, the assemblies 100, 200, 300 can be disposed within an autoinjector drug delivery device 400. Autoinjector drug delivery devices 400 can have a vertically oriented configuration with some or all drug delivery components disposed in stacked relation along a longitudinal axis L within a housing 411 of the devices 400. As a more specific example, the devices 400 can be configured to operate and inject a user with the device 400 oriented generally perpendicular to a skin surface of the user. The drug delivery components can include a reservoir 412, which can be any of the above containers 102, 202, 302a, 302b, having a fluid therapeutic 414 contained therein, a needle 420 oriented along the longitudinal axis L, and a flow path 422 fluidly coupling the reservoir 412 to the needle 420. As shown, the laser light source 104, 204, 304 can be disposed adjacent to the reservoir 412 in any of the forms discussed above. The components can further include a needle insertion mechanism 424 configured to insert the needle 420 to a desired subcutaneous depth within the user. By some approaches, the needle insertion mechanism 424 can be a retractable needle guard to expose the needle 420 or a drive mechanism to longitudinally move the needle 420 a desired distance. For example, the devices 400 can include a drive mechanism 418 configured to drive movement of the needle 420. As commonly configured, one or more of the components of the device 400, such as the drive mechanism 418 and/or needle insertion mechanism 424 and assembly 100, 200, 300, can be operable in response to actuation of a user input device 426 accessible on an exterior of the housing 411. Suitable drive mechanisms include, but are not limited to, springs, gas sources, phase changing materials, motors, or other electromechanical systems. Pursuant to this, the device 400 can include electronic components, such as a controller 428, to control operation of one or more of the drug delivery components. It will be understood that although FIG. 1 shows the components centered along the longitudinal axis L, one or more of the components can be disposed off-center from the longitudinal axis L within the housing 411 and still be considered to be in a stacked relation. In one example, an autoinjector drug delivery device having drug delivery components in a stacked relation corresponds to the reservoir 412 co-axially aligned with the needle 420. Example autoinjector devices are described in U.S. Ser. No. 62/447,174, filed Jan. 17, 2017, which is hereby incorporated by reference herein.

Figure 7:
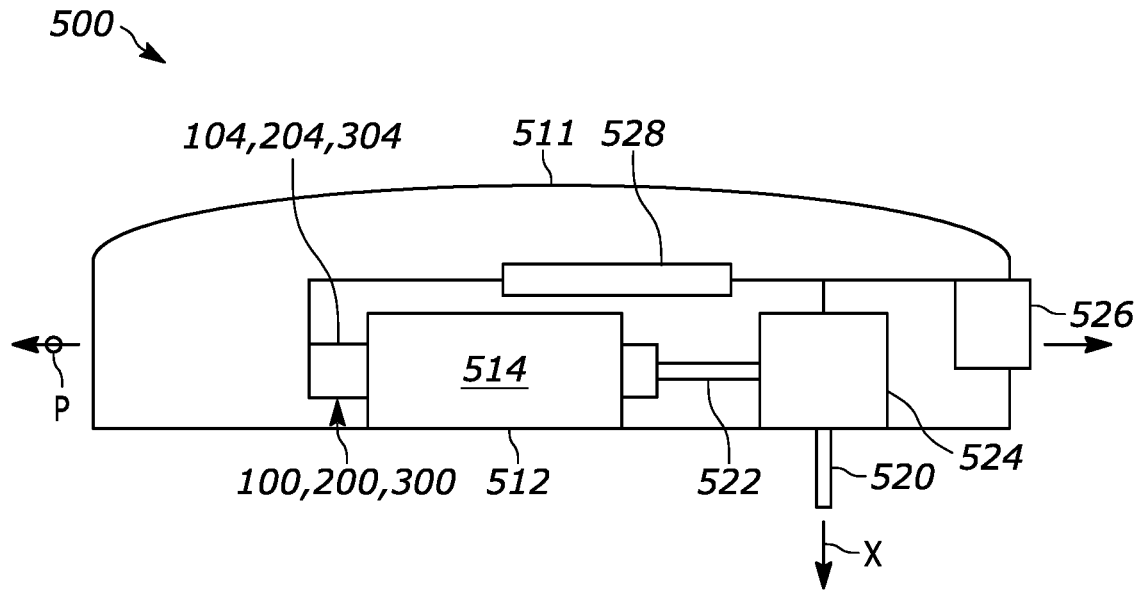
FIG. 7 is a diagrammatic view of an on-body drug delivery device.

In some versions as illustrated in FIG. 7, the assemblies 100, 200, 300 can be disposed within an on-body drug delivery device 500. On body drug delivery devices 500 can have a horizontally oriented configuration with drug delivery components disposed generally along a horizontal plane P within a housing 511 of the devices 500. With these devices 500, the housing 511 has a low profile with a larger width than height so that when a user positions the housing 511 on the skin, the components are spread out over an area of the skin rather than stacked as with the above embodiments. The drug delivery components can include a reservoir 512, which can be any of the above containers 102, 202, 302a, 302b, having a fluid therapeutic 514 contained therein, which can be removably disposed within the housing 511, a needle 520 oriented along an axis X that extends generally perpendicular to the horizontal plane P, a flow path 522 fluidly coupling the reservoir 512 to the needle 520, and a needle insertion mechanism 524 configured to insert the needle 520 to a desired subcutaneous depth within the user. As shown, the laser light source 104, 204, 304 can be disposed adjacent to the reservoir 512 in any of the forms discussed above. As commonly configured, one or more of the components of the device 500, such as the needle insertion mechanism 524 and assembly 100, 200, 300, can be operable in response to actuation of a user input device 526 accessible on an exterior of the housing 511. Pursuant to this, the device 500 can include electronic components, such as a controller 528, to control operation of one or more of the drug delivery components. Of course, it will be understood that some components can be disposed partially or entirely above or below the horizontal plane P extending generally centrally through the housing 511 and still be considered to have a horizontally oriented configuration. Suitable drive mechanisms include, but are not limited to, springs, gas sources, phase changing materials, motors, or other electromechanical systems. Example on body injector devices are described in U.S. Ser. No. 62/536,911, filed Jul. 25, 2017, which is hereby incorporated by reference herein.

Figure 8:
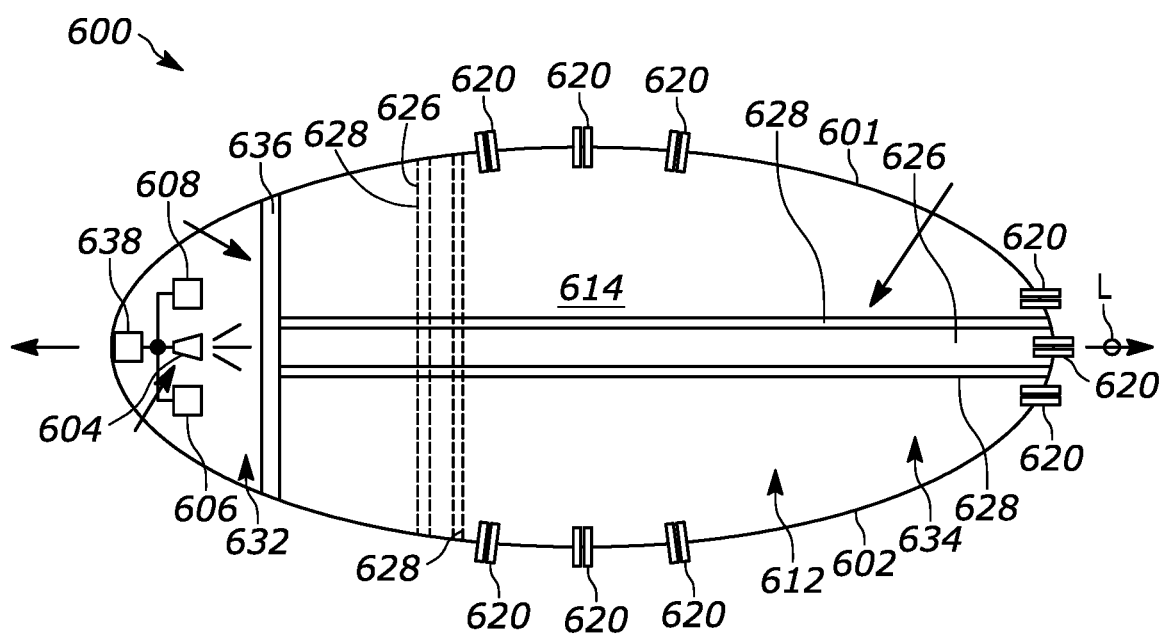
FIG. 8 is a cross-sectional view of a sixth example fluid delivery assembly including an ingestible body with an ultrasonic resonance member and a laser light source in accordance with various embodiments.

A sixth example assembly 600 is shown in FIG. 8. In this form, the assembly 600 includes an ingestible body 601 having an outer wall 602 defining an interior 612 for reception of a fluid therapeutic 614. Similar to the above forms, the assembly 600 further includes an ultrasonic resonance member 626 that extends through the interior 612 such that one or more fluid interface surfaces 628 of the ultrasonic resonance member 626 are in contact with the fluid therapeutic 614 and a laser light source 604 oriented to direct a pulsed light beam at the ultrasonic resonance member 626. As shown, the body 601 includes one or more outlets or nozzles 620 extending through the outer wall 602. The outlets 620 are disposed across a portion of the body interior 612 from the fluid interface surface 628 of the ultrasonic resonance member 626.

In the illustrated form, the body interior 612 is divided into an electronic compartment 632 and a fluid compartment 634 by an isolator wall 636 extending across the interior 612 and coupled to the outer wall 602 along an exterior edge thereof. At least a portion of the isolator wall 636 extending between the laser light source 604 and the ultrasonic resonance member 626 is transparent so that light can easily pass therethrough. For example, the separator wall can be glass or a transparent membrane dividing the electronic components of the assembly 600 from the fluid therapeutic 614. In another example, the isolator wall 636 can be the ultrasonic resonance member 626 and can extend radially across the body interior 612 to provide luminal delivery of the fluid therapeutic 614 and/or can extend longitudinally across the body interior 612 to provide radial delivery of the fluid therapeutic 614.

As shown, the assembly 600 can further include a power source 606 to provide power to the laser light source 604 and a controller 608 to selectively energize the laser light source 604. In one form, the controller 608 can be configured to energize the laser light source 604 after a predetermined amount of time has passed. For example, the controller 608 can begin a countdown after reception of a signal from an external device. In another form, the assembly 600 can include a pH sensor 638 that is disposed within or mounted to the body 601 and is configured to measure a pH of an environment surrounding the body 601. With the pH sensor 638, the controller 608 can determine when the body 601 passes through the stomach of a patient, which has a pH of 1.5 to 3.5, and further into the digestive tract. For example, the intraluminal pH is about pH 6 in the duodenum and gradually increases in the small intestine to about pH 7.4 in the terminal ileum. As such, the controller 608 can be configured to energize the laser light source 604 to cause the fluid therapeutic 614 to be driven through the outlets 620 at a predetermined pH, such as 6 or 7.

The ultrasonic resonance member 626 can take any desired shape. In one example, the ultrasonic resonance member 626 can have a plate configuration and the fluid interface surface 628 can correspond to the front and back main surfaces of the plate body. This configuration will result in the fluid therapeutic being driven to opposite sides of the body 601. In another example, the ultrasonic resonance member 626 can have a rod configuration, such that the fluid interface surface 628 is an annular outer surface of the rod. With this configuration, the fluid therapeutic 618 is driven radially outwardly from the rod. With either configuration, the ultrasonic resonance member 626 can extend longitudinally within the body 601 so that the fluid interface surface or surfaces 628 are aligned with radial outlets 620. In an alternative form, the ultrasonic resonance member 626 can extend transverse to a longitudinal axis L of the body 601, such that the fluid interface surface 628 is aligned with an axial outlet 620 for luminal delivery. With these configurations, the fluid therapeutic 618 can be dispensed to target inflamed or diseased tissues luminally within GI-tract or for systemic radial delivery to ensure crossing of the mucosa of the intestine. Any desired number of outlets 620 can be utilized to achieve a desired delivery profile.

In one example, when an LED laser having a predetermined wavelength of 527 nm wavelength was operated to direct a pulsed light beam at 0.5 ms or shorter period with a pulse width of 150 nm was directed to a gold implanted quartz glass ultrasonic resonance member, a narrow jet stream of fluid within the fluidic container is created. For this configuration, an estimated flow pressure in the range of −10 to +10 kPa can be achieved.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); Ova-Rex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-yl-carbamoyl)-2-phenylethyl)-2-((S)-2-(2-morpholinoacet-amido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfo-nyl)ethyl]-2,3-dihydro-1,3-dioxo-1H-isoindol-4-yl]acet-amide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33× anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)× anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33× anti-CD3 BiTE® (bispecific T cell engager) construct. In some embodiments, the drug delivery device may contain or be used with AMG 701 or another product containing a half-life extended (HLE) anti-B-cell maturation antigen (BCMA)× anti-CD3 BiTE® (bispecific T cell engager) construct. In some embodiments, the drug delivery device may contain or be used with AMG 757 or another product containing a half-life extended (HLE) anti-delta-like ligand 3 (DLL3)× anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. An ingestible fluid delivery device comprising:
   a body including one or more walls defining an interior and having one or more outlets extending through the one or more walls;
   an ultrasonic resonance member comprising a treated substrate having a fluid interface surface;
   a laser light source oriented to direct a pulsed light beam at the ultrasonic resonance member to urge a fluid therapeutic disposed within the interior into a jet stream;
   a controller configured to control operation of the laser light source; and
   an isolator extending across the interior of the body to divide the interior into a laser compartment and a fluid compartment, wherein the one or more outlets extend through the one or more walls into the fluid compartment and the laser light source is disposed within the laser compartment.

2. The ingestible fluid delivery device of claim 1, wherein the ultrasonic resonance member comprises either (a) a plate, the fluid interface surface comprises at least one of a plurality of main surfaces of the plate, and the one or more outlets are aligned with the fluid interface surface across a portion of the interior, or (b) a rod, the fluid interface surface comprises an annular outer surface of the rod, and the one or more outlets are aligned radially outward of the rod across a portion of the interior.

3. The ingestible fluid delivery device of claim 1, wherein the laser light source is configured to direct a pulsed light beam at the ultrasonic resonance member through the isolator.

4. The ingestible fluid delivery device of claim 1, wherein the laser light source is configured to direct a pulsed light beam at the isolator to urge the fluid therapeutic into a jet stream.

5. The ingestible fluid delivery device of claim 1, further comprising a pH sensor; and
   wherein the controller is configured to activate the laser light source in response to the pH sensor determining that the body is in an environment having a pH value above a predetermined threshold.

6. The ingestible fluid delivery device of claim 1, wherein the one or more outlets are oriented (a) along a longitudinal axis of the body to provide a luminal delivery of the fluid, and/or (b) transverse to a longitudinal axis of the body to provide a radial delivery of the fluid.

7. The ingestible fluid delivery device of claim 1, wherein the treated substrate of the ultrasonic resonance member comprises a treated glass substrate.

8. A drug delivery device comprising:
   a container defining an interior with an outlet, the interior defined by at least one wall;
   an ultrasonic resonance member comprising at least a portion of the at least one wall of the container, the ultrasonic resonance member comprising a treated substrate and having a fluid interface surface in contact with a fluid therapeutic disposed within the interior, the fluid interface surface aligned with the outlet of the container; and
   a laser light source oriented and configured to direct a pulsed light beam at the ultrasonic resonance member to urge a fluid therapeutic disposed within the container into a jet stream,
   wherein the laser light source comprises an array of laser light sources, the array including a plurality of laser light sources disposed about a circumference of the container and configured to be sequentially activated around the circumference to create a vortex in a therapeutic fluid in the container and a central laser light source configured to direct the vortex toward the outlet.

9. The drug delivery device of claim 8, wherein the treated substrate of the ultrasonic resonance member comprises a treated glass substrate.

10. A drug delivery device comprising:
    a first container defining an interior with an outlet;
    a first ultrasonic resonance member, the first ultrasonic resonance member comprising a treated substrate and having a fluid interface surface in contact with a fluid therapeutic disposed within the interior, the fluid interface surface aligned with the outlet of the first container;
    a laser light source oriented and configured to direct a pulsed light beam at the ultrasonic resonance member to urge a fluid therapeutic disposed within the container into a jet stream;
    a second container defining an interior with an outlet; and
    a second ultrasonic resonance member comprising a treated substrate having a fluid interface surface in contact with a fluid therapeutic disposed within the interior of the second container, the fluid interface surface of the second ultrasonic resonance member aligned with the outlet of the second container, wherein the outlets of the first and second containers are fluidly connected by a combined conduit.

11. The drug delivery device of claim 10, wherein the laser light source comprises a first laser light source; and further comprising a second laser light source, the second laser light source oriented and configured to direct a pulsed light beam into the second ultrasonic resonance member to urge a fluid therapeutic disposed within the second container into a jet stream.

12. The drug delivery device of claim 11, wherein the fluid therapeutics disposed within the interiors of the first and second containers comprise a first fluid therapeutic and a second fluid therapeutic; and vortices generated by the jet streams within the first and second containers mix the first and second fluid therapeutics together to deliver a mixture.

13. The drug delivery device of claim 11, wherein vortices generated by the jet streams within the first and second containers reconstitute a lyophilized drug compound using a diluent solution.

14. The drug delivery device of claim 10, wherein the first and second ultrasonic resonance members comprise a single-piece plate member; and the laser light source is oriented to direct a pulsed light beam along a longitudinal axis of the single-piece plate member to urge fluid therapeutics disposed within the first and second containers into jet streams to drive the fluid therapeutics through the outlets of the first and second containers, respectively, mixing the fluid therapeutics together.

15. The drug delivery device of claim 14, wherein the fluid therapeutics disposed within the interiors of the first and second containers comprise a first fluid therapeutic and a second fluid therapeutic, the second fluid therapeutic being different than the first fluid therapeutic.

16. The drug delivery device of claim 10, wherein the treated substrate of the second ultrasonic resonance member comprises a treated glass substrate.

\* \* \* \* \*